(12) United States Patent
Nair et al.

(10) Patent No.: US 9,439,583 B2
(45) Date of Patent: Sep. 13, 2016

(54) FUNCTIONAL ASSESSMENT AND TREATMENT CATHETERS AND METHODS FOR THEIR USE IN THE LUNG

(71) Applicant: Pulmonx Corporation, Redwood City, CA (US)

(72) Inventors: Ajit Nair, Milpitas, CA (US); Son Gia, San Jose, CA (US); Roger Farhnoltz, Fremont, CA (US); Nikolai Aljuri, Hillsborough, CA (US)

(73) Assignee: Pulmonx Corporation, Redwood City, CA (US)

( * ) Notice: Subject to any disclaimer, the term of this patent is extended or adjusted under 35 U.S.C. 154(b) by 386 days.

(21) Appl. No.: 13/689,344

(22) Filed: Nov. 29, 2012

(65) Prior Publication Data

US 2013/0338524 A1    Dec. 19, 2013

Related U.S. Application Data

(62) Division of application No. 11/845,296, filed on Aug. 27, 2007, now Pat. No. 8,342,182.

(60) Provisional application No. 60/828,496, filed on Oct. 6, 2006, provisional application No. 60/823,734, filed on Aug. 28, 2006.

(51) Int. Cl.
*A61M 16/04* (2006.01)
*A61M 25/01* (2006.01)
(Continued)

(52) U.S. Cl.
CPC ............... *A61B 5/085* (2013.01); *A61B 5/097* (2013.01); *A61B 5/4836* (2013.01);
(Continued)

(58) Field of Classification Search
CPC ........... A61M 25/01; A61M 25/0102; A61M 25/04; A61M 2025/0681; A61M 2025/1081; A61M 16/00; A61M 29/00; A61B 17/12022; A61B 12/12136; A61B 17/12036; A61B 17/1204; A61B 17/12131; A61B 17/12168; A61B 17/24; A61B 17/3439; A61B 2017/1205; A61B 2017/242; A61B 2017/3484; A61B 2017/22067; A61B 2017/22069; A61B 2017/3488; A61F 2/04; A61F 2/043; A61F 2/82; A61F 2/88; A61F 2/90; A61F 2/95; A61F 2/958
USPC ....... 128/200.24, 207.14–207.16; 604/96.01, 604/104, 107; 606/191, 195, 198
See application file for complete search history.

(56) References Cited

U.S. PATENT DOCUMENTS 2,230,226 A * 2/1941 Auzin ............................ 604/104
4,921,484 A * 5/1990 Hillstead ...................... 604/104
(Continued)

FOREIGN PATENT DOCUMENTS

EP    0791340 A1    8/1997
EP    0815803 A1    1/1998
(Continued)

OTHER PUBLICATIONS

Choostenttm, Covered Esophageal Stent, pp. 1-2, Jul. 26, 2005.
(Continued)

*Primary Examiner* — Lynne Anderson
*Assistant Examiner* — Kathryn E Ditmer
(74) *Attorney, Agent, or Firm* — Wilson Sonsini Goodrich & Rosati

(57) ABSTRACT

Lung conditions are diagnosed and optionally treated using a functional assessment catheter or a functional lung assessment and treatment catheter. A flow restrictive component is initially placed in a bronchus or lung passageway upstream from a diseased lung region. The isolated lung region is then functionally assessed through the catheter, while the flow restrictive component remains in place. If the patient is a good candidate for treatment by occlusive or restrictive treatment techniques, the flow resistive component may be left in place. If the patient is not suitable for such treatment, the flow resistive component may be removed.

12 Claims, 14 Drawing Sheets

(51) Int. Cl.

| | | |
|---|---|---|
| *A61B 5/08* | (2006.01) | |
| *A61B 5/097* | (2006.01) | |
| *A61B 5/085* | (2006.01) | |
| *A61M 25/00* | (2006.01) | |
| *A61M 25/06* | (2006.01) | |
| *A61B 5/00* | (2006.01) | |
| *A61B 17/12* | (2006.01) | |
| *A61F 2/04* | (2013.01) | |

(52) U.S. Cl.
CPC ...... *A61B 5/6853* (2013.01); *A61B 17/12104* (2013.01); *A61M 16/04* (2013.01); *A61M 16/0406* (2014.02); *A61M 25/0075* (2013.01); *A61M 25/0662* (2013.01); *A61F 2002/043* (2013.01); *A61M 2025/0004* (2013.01); *A61M 2025/0681* (2013.01)

(56) References Cited

U.S. PATENT DOCUMENTS

| | | | |
|---|---|---|---|
| 5,261,916 A * | 11/1993 | Engelson | A61B 17/12022 604/171 |
| 5,304,195 A * | 4/1994 | Twyford, Jr. | A61B 17/12022 604/907 |
| 5,624,449 A | 4/1997 | Pham et al. | |
| 5,649,906 A | 7/1997 | Gory et al. | |
| 5,749,883 A * | 5/1998 | Halpern | 606/159 |
| 5,795,322 A | 8/1998 | Boudewijn | |
| 5,800,455 A | 9/1998 | Palermo et al. | |
| 5,895,391 A * | 4/1999 | Farnholtz | A61B 17/12022 606/108 |
| 6,099,546 A | 8/2000 | Gia | |
| 6,179,860 B1 * | 1/2001 | Fulton et al. | 606/200 |
| RE37,117 E | 3/2001 | Palermo | |
| 6,287,290 B1 | 9/2001 | Perkins et al. | |
| 6,371,971 B1 | 4/2002 | Tsugita et al. | |
| 6,527,761 B1 * | 3/2003 | Buch et al. | 604/516 |
| 6,635,068 B1 * | 10/2003 | Dubrul et al. | 606/200 |
| 6,679,264 B1 | 1/2004 | Deem et al. | |
| 6,722,360 B2 | 4/2004 | Doshi | |
| 6,941,950 B2 | 9/2005 | Wilson et al. | |
| 6,958,074 B2 * | 10/2005 | Russell | A61F 2/01 600/585 |
| 6,997,918 B2 | 2/2006 | Soltesz et al. | |
| 7,011,094 B2 | 3/2006 | Rapacki et al. | |
| 8,342,182 B2 | 1/2013 | Nair et al. | |
| 2001/0037808 A1 | 11/2001 | Deem et al. | |
| 2002/0143387 A1 | 10/2002 | Soetikno et al. | |
| 2002/0169494 A1 * | 11/2002 | Mertens et al. | 623/1.11 |
| 2003/0051733 A1 * | 3/2003 | Kotmel | A61B 5/0813 128/207.14 |
| 2003/0154988 A1 | 8/2003 | DeVore et al. | |
| 2004/0060563 A1 * | 4/2004 | Rapacki et al. | 128/207.14 |
| 2004/0073191 A1 | 4/2004 | Soltesz et al. | |
| 2004/0206349 A1 * | 10/2004 | Alferness et al. | 128/200.24 |
| 2005/0288684 A1 * | 12/2005 | Aronson et al. | 606/108 |
| 2006/0095002 A1 | 5/2006 | Soltesz et al. | |
| 2006/0102186 A1 | 5/2006 | Adler | |
| 2006/0122647 A1 | 6/2006 | Callaghan et al. | |
| 2006/0135986 A1 * | 6/2006 | Wallace | A61B 17/12113 606/200 |
| 2006/0264772 A1 | 11/2006 | Aljuri et al. | |
| 2006/0271093 A1 * | 11/2006 | Holman et al. | 606/194 |
| 2007/0005083 A1 | 1/2007 | Sabanathan et al. | |
| 2007/0096048 A1 | 5/2007 | Clerc | |
| 2007/0142742 A1 | 6/2007 | Aljuri et al. | |
| 2007/0186933 A1 * | 8/2007 | Domingo et al. | 128/207.15 |
| 2007/0225747 A1 * | 9/2007 | Perkins et al. | 606/195 |

FOREIGN PATENT DOCUMENTS

| | | |
|---|---|---|
| WO | WO 03/022124 A2 | 3/2003 |
| WO | WO 03/022221 A2 | 3/2003 |
| WO | WO 2006/055692 A2 | 5/2006 |
| WO | WO 2006/078451 A1 | 7/2006 |

OTHER PUBLICATIONS

European search report dated Jul. 28, 2009 fpr EP Application No. 07841495.0.

International search report and written opinion dated Apr. 8, 2008 for PCT/US2007/077023.

Office action dated Feb. 8, 2012 for U.S. Appl. No. 11/845,296.

Office action dated Apr. 13, 2011 for U.S. Appl. No. 11/845,296.

* cited by examiner

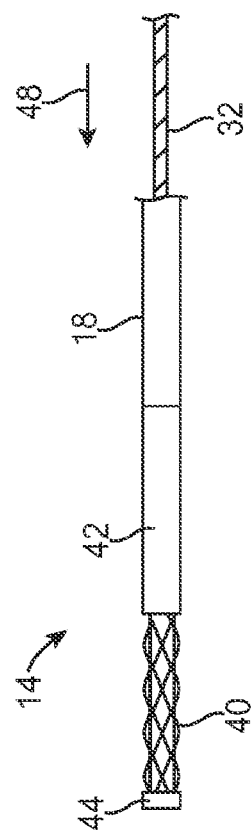
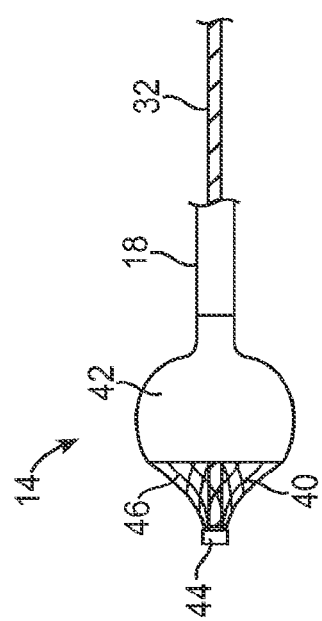
FIG. 2B
FIG. 2A

FUNCTIONAL ASSESSMENT AND TREATMENT CATHETERS AND METHODS FOR THEIR USE IN THE LUNG

CROSS-REFERENCES TO RELATED APPLICATIONS

This application is a divisional of U.S. patent application Ser. No. 11/845,296, filed Aug. 27, 2007, which claims priority to Provisional Application No. 60/823,734, filed Aug. 28, 2006, and Provisional Application No. 60/828,496, filed Oct. 6, 2006, the disclosures of which are incorporated herein by reference.

BACKGROUND OF THE INVENTION

1. Field of the Invention

The present invention relates generally to medical methods and apparatus. More particularly, the present invention relates to methods and apparatus for the assessment and treatment of lung diseases, such as chronic obstructive pulmonary disease, by detecting the status of the disease and determining an appropriate treatment protocol.

Chronic obstructive pulmonary disease (COPD) is a significant medical problem affecting sixteen million people or about 6% of the U.S. population. Specific diseases in this group include chronic bronchitis, asthmatic bronchitis, and emphysema. While a number of therapeutic interventions are used and have been proposed, none are completely effective, and COPD remains the fourth most common cause of death in the United States. Thus, improved and alternative treatments and therapies would be of significant benefit.

Management of COPD is largely medical and infrequently surgical. Initially, exercise and smoking cessation are encouraged. Medications including bronchodilators and anti-inflammatories are routinely prescribed. Pulmonary rehabilitation has been shown to improve quality of life and sense of well being. Long term oxygen is generally reserved for the more severely affected patients.

Emphysema is a condition of the lung characterized by the abnormal permanent enlargement of the airspaces distal to the terminal bronchiole, accompanied by the destruction of their walls. It is known that emphysema and other pulmonary diseases reduce the ability of part of the lungs to fully expel air during the exhalation phase of the breathing cycle. During breathing, the diseased portion of the lung does not fully recoil due to the diseased lung tissue being less elastic than healthy tissue. Consequently, as the airways normally held open by the elastic pull of the lungs become floppy and the diseased lung tissue exerts a diminished driving force during exhalation, the airways close prematurely resulting in air trapping and hyperinflation.

In addition, hyper-expanded lung tissue occupies more of the pleural space than healthy lung tissue. In most cases, only a part of the lung is diseased while the remaining portion is relatively healthy and therefore still able to efficiently carry out oxygen exchange. By taking up more of the pleural space, the hyper-expanded lung tissue reduces the space available to accommodate the healthy, functioning lung tissue. As a result, the hyper-expanded lung tissue causes inefficient breathing by compressing the adjacent functional airways, alveolar units, and capillaries in relatively healthier lung tissue.

Lung function in patients suffering from some forms of COPD can be improved by reducing the effective lung volume, typically by resecting diseased portions of the lung. Resection of diseased portions of the lungs both promotes expansion of the non-diseased regions of the lung and decreases the portion of inhaled air which goes into the lungs but is unable to transfer oxygen to the blood. Accordingly, recruitment of previously compressed functional airways, alveolar units, and capillaries in relatively healthier lung is possible resulting in more gas exchange in addition to better matching of lung and chest wall dimensions. Lung reduction is conventionally performed in open chest or thoracoscopic procedures where the lung is resected, typically using stapling devices having integral cutting blades.

While effective in many cases, conventional lung volume reduction surgery (LVRS) is significantly traumatic to the patient, even when thoracoscopic procedures are employed. Such procedures often result in the unintentional removal of healthy lung tissue, and frequently leave perforations or other discontinuities in the lung which result in air leakage from the remaining lung. Even technically successful procedures can cause respiratory failure, pneumonia, and death. In addition, many older or compromised patients are not able to be candidates for these procedures.

As an alternative to LVRS, endobronchial volume reduction (EVR) uses endobronchially introduced devices which plug or otherwise isolate a diseased compartment from healthier regions of the lung in order to achieve volume reduction of the diseased compartment. Isolation devices may be implanted in the main airways feeding the diseased region of the lung, and volume reduction takes place via absorption atelectasis after implantation or via collapse by actively suctioning of the target compartment prior to implantation. These implanted isolation devices can be, for example, self-expanding occlusive stents that prevent air flow in both directions or one-way valves that allow flow in the exhalation direction only.

While a significant improvement over LVRS, EVR can have a limited therapeutic benefit when the treated region in the lung is exposed to collateral ventilation from adjacent regions. The lungs comprise a plurality of compartments, referred to as lung compartments or lobes, which are separated from one another by a double layer of enfolded reflections of visceral pleura, referred to as fissures. While the fissures which separate the compartments are typically impermeable, in patients suffering from COPD, the fissures are frequently incomplete, leaving a pathway for collateral airflow or inter-lobular collateral ventilation. Such collateral airflow can result in the intrusion of air into the isolated lung compartments treated by LVR, thus reducing or eliminating the desired volume reduction.

While collateral flow to diseased lung compartments can be detected, for example using the methods described in copending, commonly-owned U.S. patent application Ser. No. 11/296,591, filed on Dec. 7, 2005 (US 2006/0264772A1) and Ser. No. 11/550,660, filed on Oct. 18, 2006 (US 2007/0142742A1). While the use of these procedures can identify patents likely to benefit from EVR procedures, the need to perform a separate diagnostic procedure prior to a therapeutic procedure is time consuming, costly, and inconvenient for the patient.

For these reasons, it would be desirable to provide alternative and improved methods and apparatus for performing endobronchial volume reduction (EVR) and other lung therapies in an efficient and effective manner. In particular, it would be desirable to provide methods and apparatus which permit both the detection of collateral ventilation and subsequent treatment of diseased lung compartments in a single protocol where the treatment is completed only for those patients having no or an acceptable level of collateral ventilation. At least some of these objectives will be met by the inventions described hereinbelow.

2. Description of the Background Art

Exemplary methods for treating diseased lung compartments by isolating the diseased regions are described, for example, in U.S. Pat. No. 6,287,290; U.S. Pat. No. 6,679,264; U.S. Pat. No. 6,722,360; U.S. Pat. No. 7,011,094; and printed publication U.S. 2007/0005083. Methods for detecting collateral ventilation prior to treatment of diseased lung regions are described in patent publications U.S. 2006/0264772A1 and U.S. 2007/0142742A1, the full disclosures of which have been previously incorporated herein by reference.

BRIEF SUMMARY OF THE INVENTION

The present invention provides improved methods and apparatus for treating targeted lung compartments, typically diseased lung compartments, in patients suffering from emphysema or other forms of COPD. The methods allow for both detecting collateral ventilation in the target lung compartment and for treating the target lung compartment in a single protocol, thus reducing the time and expense necessary for treating patients and providing a more convenient and acceptable therapy for the patient.

The methods utilize a catheter having a flow restrictive component connected thereto, typically at a distal end. The flow restrictive component is deployed in a main bronchus which feeds the target lung compartment while said component is connected to the catheter. While the target lung compartment remains isolated by the flow restrictive component, a determination is made of whether collateral ventilation exists in the target lung compartment. Any of the protocols described in published applications U.S. 2006/0264772 or U.S. 2007/0142742, both of which have been previously incorporated herein by reference, may be employed.

If it is determined that collateral ventilation is not present in the target lung compartment, the flow restrictive component may be detached from the catheter and left in place to effect a permanent isolation of the compartment to complete what is likely to be a successful LVR therapy. If, on the contrary, collateral ventilation is found to exist to a degree which would make successful LVR treatment unlikely, the flow restrictive component will be left attached to the catheter, and the catheter may be used to withdraw the flow restrictive element from the lung. The patient may then be treated by other therapies. By using the flow restrictive element both for the detection of collateral ventilation and for the optional treatment using EVR protocols, treatment time is reduced and the patient's comfort is increased.

The flow restrictive component may be the same as or similar to many components already described in the patent and medical literature. That is, a flow restrictive element may be intended to effect a complete blockage of flow into and out of the isolated lung compartment. Such blocking elements may be referred to as "occlusive stents," and are described in commonly-assigned U.S. Pat. No. 6,527,761 and U.S. Pat. No. 6,997,918, the full disclosures of which are incorporated herein by reference. Alternatively, the flow restrictive elements may comprise a restrictor which includes a small orifice, small diameter tube, perforated membrane, densely braided structure, perimeter channel, or other fixed-resistance element which impedes flow, but allows a low flow in both directions. Such flow-permitting restrictors are referred to as "restrictor stents," and are described in copending application Ser. No. 11/682,986, the full disclosure of which is incorporated herein by reference.

Regardless of whether an occlusive stent is used or a restrictive stent is used, it will usually be necessary that the flow restrictor provide for a flow path from the catheter to the isolated lung compartment to permit performance of the diagnostic test for collateral ventilation. The tests described in the previously incorporated patent applications generally rely on detecting flow from the isolated compartment or introducing gas into the isolated compartment in order to determine compliance. Thus, while used in the diagnostic or determining mode, it will usually be necessary that the flow restrictor have the ability to allow gas flow into and/or out of the compartment.

Flow restrictive elements or components which allow for flow therethrough can be provided in a number of ways. For example, the restrictive stents described in application Ser. No. 11/682,986 each have an orifice, lumen, or other flow channel present therein which can be relied on for gas exchange in the methods of the present invention. In the case of occlusive stents, it is possible to provide for a temporary orifice or flow path therethrough which can be sealed when the flow restrictive element is detached from the delivery catheter.

The present invention further provides functional assessment catheters comprising a catheter shaft and a flow restrictive component thereon. The catheter shaft has a distal end, a proximal end, and a central passage therebetween. The flow restrictive component is disposed on or at the distal end of the catheter shaft and has an expanded configuration and a contracted configuration.

In a first embodiment, a separate obturator is disposed in the central passage of the catheter shaft and is shiftable between a distally advanced position and a proximally retracted position. In the distally advanced position, the distal end of the obturator engages and elongates the flow restrictive component which causes the component to assume the contracted configuration. By proximally retracting the obturator, the flow restrictive component is allowed to resume or "spring back" to its expanded configuration. Thus, the flow restrictive component can be delivered to the bronchus feeding the lung compartment by first advancing the component in its contracted configuration with the obturator advanced and then deploying the component by retracting the obturator to allow the flow restrictive component to expand in situ at a desired location immediately upstream of the target lung compartment.

In this first embodiment, the functional assessment catheter may have a permanently attached flow restrictive element, in which case it is useful only for performing the diagnostic function and not for releasing the flow restrictive element to treat the patient. To use the catheter in a therapeutic situation, additional means for separating flow restrictive element from the catheter shaft would be provided.

In a second embodiment, a functional assessment and treatment catheter is specifically designed to permit release of the flow restrictive component from the catheter shaft. The flow restrictive component is secured to a distal end of the catheter shaft by a selective release mechanism. A wide variety of suitable selective release mechanisms are available, including mechanical mechanisms, such as screws, lock and release mechanisms, spiral screw mechanisms, shape memory release mechanisms, collets, latches, jaws, and the like. Electrical and electromechanical release mechanisms would also be available, including piezoelectric detachment mechanisms, electrical heating and expansion release mechanisms, and the like. Additionally, magnetic release mechanisms would be available. A variety of release mechanisms of the type used in embolic coil release would be useful in the release structures of the present invention. Such release mechanisms are described, for example, in U.S. Pat. Nos. RE37/117; 6,099,546; 5,800,455; and 5,624,449; the full disclosures of which are incorporated herein by reference.

In both the releasable and nonreleasable flow restrictive component embodiments, the flow restrictive component will preferably comprise a resilient scaffold having an elastomeric covering over at least a portion thereof. Usually, the resilient scaffold comprises counterwound helical supports formed from stainless steel, spring steel with coating, memory polymers, nickel-titanium alloys, and the like. The elastomeric covering can be formed from a variety of polymers, including silicones, polyurethanes, polyethylenes, polyvinylchlorides, and the like.

BRIEF DESCRIPTION OF THE DRAWINGS

FIGS. 2A and 2B illustrate the flow restrictive component of FIG. 1 in both the expanded (FIG. 2A) and contracted (FIG. 2B) configurations.

DETAILED DESCRIPTION OF THE INVENTION

Figure 1:
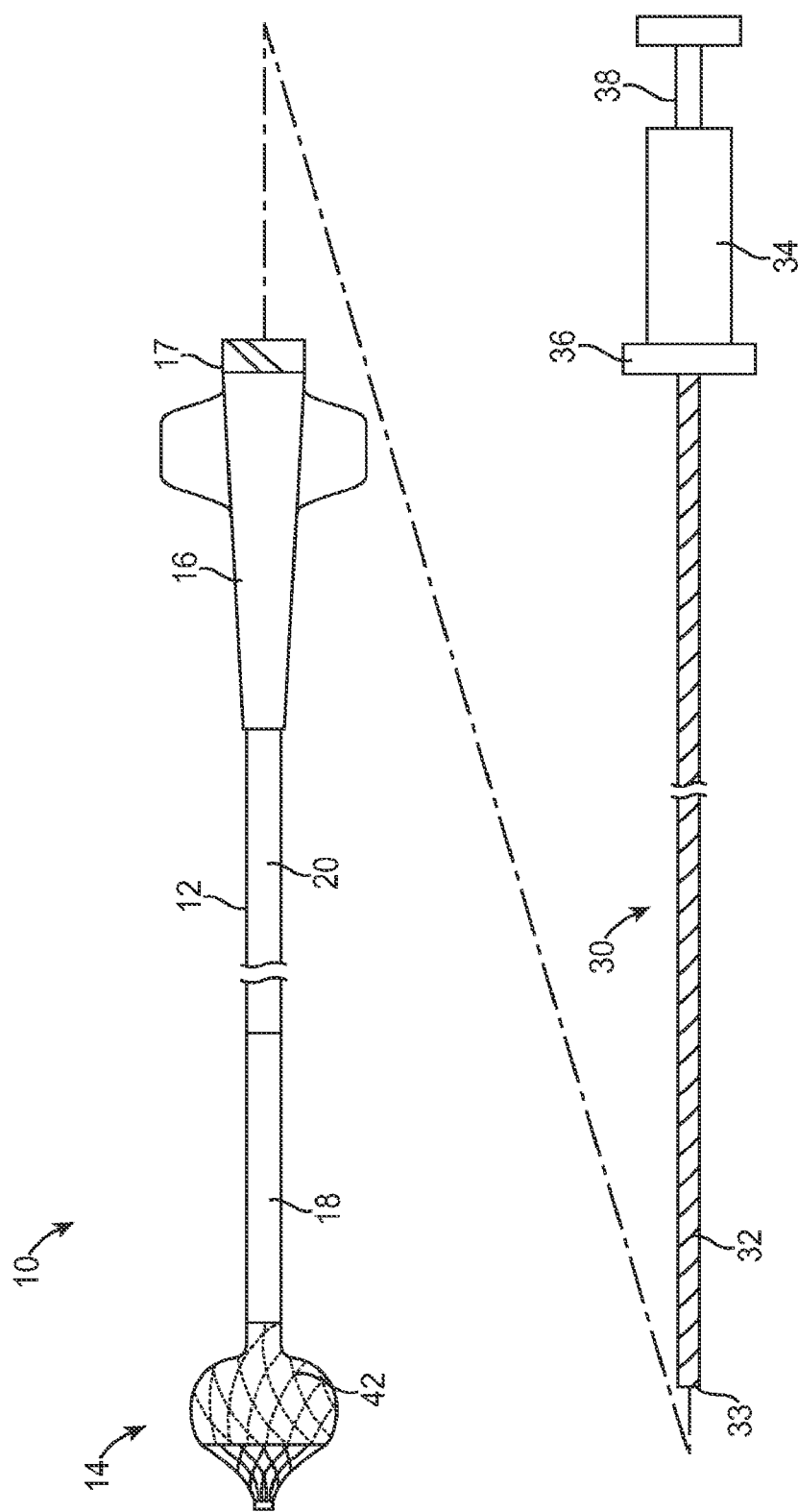
FIG. 1 illustrates a functional assessment catheter of the present invention, employing an obturator for expanding and contracting a flow resistive component.

As shown in FIG. 1, a functional assessment catheter 10 constructed in accordance with the principles of the present invention comprises a shaft 12 having a flow restrictive component 14 attached at its distal end and a hub assembly 16 attached at its proximal end. The shaft 12 will have dimensions and mechanical properties suitable for transbronchial introduction into the passageways of the lung, typically where the flow restrictive component 14 may be placed into the branching bronchii of the lung and advanced to locations in the main bronchus feeding a target lung compartment. Usually, the shaft will comprise a braid-reinforced polymer, such as a polyvinylchloride, a polytetrafluoroethylene (PTFE), a polypropylene, a polyethylene terephthalate (PET), a polyurethane, a polyurethane/polycarbonate mixture, or any one of a variety of other suitable polymers. In a specific embodiment, a catheter shaft will comprise a relatively soft distal region 18 and a relatively harder proximal region 20. For example, the distal region can be formed from a 55D durometer polyethylene block polyamide (PEBAX) and the proximal region 20 can be formed from a 72D durometer PEBAX.

The flow restrictive component 14 will normally be in an expanded configuration, as shown in FIGS. 1 and 2A, but may be axially elongated in order to assume a contracted or narrow diameter configuration, as shown in FIG. 2B. The component 14 will typically comprise a scaffold structure 40, typically formed from counterwound helical elements, covered at least partially by an elastomeric covering 42. The individual helical elements will be formed from an elastic material, typically an elastic metal but optionally a shape memory polymer. Suitable elastic metals include stainless steel, spring stainless steel, nickel-titanium alloy, and the like. In an exemplary embodiments, the elastic elements are made from 0.125 mm nitinol wires counterwound into a braid. The individual nitinol wires are joined at a distal end by end cap 44 and are connected at their proximal ends to the distal end of the distal region 18 of the shaft 12. Alternatively, the scaffold structure could be made by chemically etching a thin layer of a suitable elastic metal and forming into the shape of the restrictive component. The membrane can be made from any of the materials described earlier, and in the exemplary embodiment will be formed from a silicone formed over the proximal portion of the scaffold 40 and extending over the mid-section of the scaffold, leaving a distal region 46 of the scaffold open. While the distal region is open, the mid-section of the flow restrictive component 14 will be able to engage the interior of the bronchus in which it is expanded in order to form a tight seal, at least while the flow restrictive component 14 remains attached to the shaft 12.

In the particular embodiment illustrated in FIGS. 1, 2A, and 2B, the flow restrictive component 14 is intended to remain fixed to the shaft 12, so the catheter 10 is intended only for assessment, not for therapy. It will be appreciated that this structure could be modified, or a separate releasing device could be provided in order to detach the flow restrictive component 14 from the shaft in order to leave the component in place should the patient be a good candidate for therapy. Other embodiments of the catheter, described hereinafter, are shown with specific detachment means for use in both diagnostic and therapeutic applications.

An obturator assembly 30 is provided in order to elongate and constrict the diameter of the flow restrictive component 14. The obturator assembly 30 comprises a flexible rod 32, typically a coiled wire formed from a metal or semi-rigid plastic material. Suitable metals include stainless steel, titanium, nickel-titanium alloy, or any other metal of the type conventionally used in construction of medical guidewires. Metal shafts may be coated with PTFE or other material in order to enhance the lubricity as it is introduced through a lumen of the shaft 12 into the interior of the flow restrictive component 14. A distal tip 33 engages the end cap 44 of the flow restrictive component 14, as best seen in FIG. 2A. By axially advancing the rod 32, the end cap 44 is translated distally, thus axially elongating the flow restrictive component 14 and reducing its diameter, as best seen in FIG. 2B. Conveniently, an advancement actuator 34 may be connected to a proximal end of the rod 32. As illustrated in FIG.

1, the actuator 34 may comprise a connector 36 which is mountable on a luer or other fitting 17 on proximal hub 16. Once the actuator 34 is attached to the hub 16, a plunger 38 may be depressed in order to advance the rod 32 in the direction of arrow 48 in FIG. 2B. Optionally, a detent or other locking mechanism may be provided in the actuator 34 in order to hold the flow restrictive component 14 in its narrow diameter configuration during introduction into the bronchii. By releasing the plunger 18, the spring force in the flow restrictive component 14 will push the rod 32 proximally and allow the component to reassume its expanded or large diameter configuration within the main bronchus leading to the target lung compartment.

Figure 3:
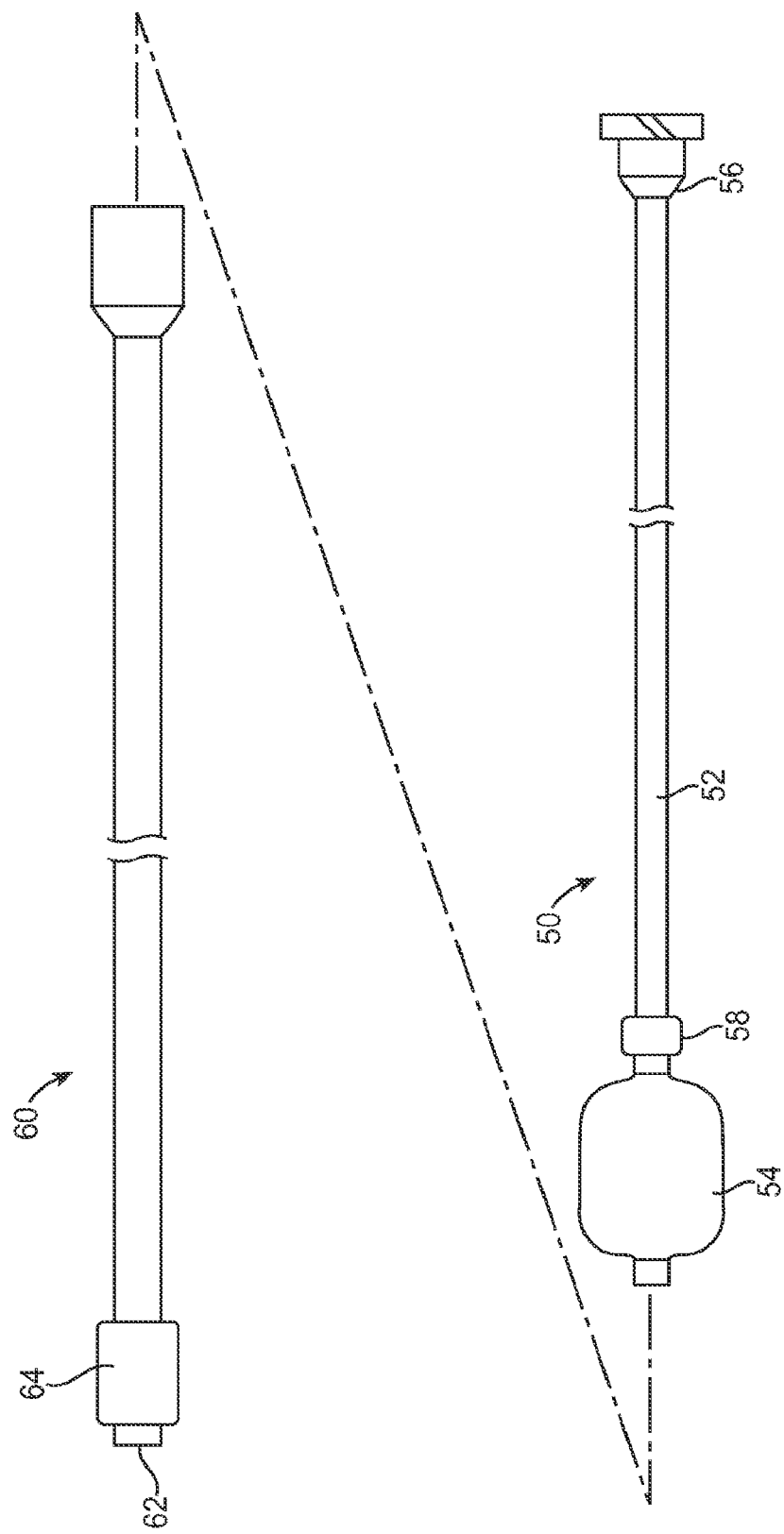
FIG. 3 illustrates a functional assessment and therapy catheter of the present invention, where the flow restrictive component is detachable and is constrained during delivery by an outer tubular delivery member.

Referring now to FIG. 3, a functional assessment and therapy catheter 50 will be described. The catheter 50 differs from the functional assessment catheter 10 described previously in that it is adapted to selectively release a flow restrictive component 54 from a distal end of a catheter shaft 52. In particular, a release mechanism 58 is formed or otherwise provided at a proximal end of the flow restrictive component 54. The release mechanism 58 may take any of a wide variety of forms, including mechanical, electrical, chemical (e.g., dissolvable), or combinations thereof. The release mechanism 58 will retain the flow restrictive component 54 firmly on the distal end of the shaft 52 until such a time as it may be desired to release the component within a bronchii. While the flow restrictive component 54 remains attached to the shaft, a flow path will remain between a lumen in the shaft 52 and a passage, lumen, open interior, or other provision within the flow restrictive component which permits gas exchange between the lumen and the shaft 52 and a distal region of the flow restrictive component 54. The ability to permit gas exchange through the catheter shaft 52 and flow restrictive component 54 is desirable to allow performance of collateral ventilation or other diagnostic procedures while the flow resistive component 54 is expanded within the bronchii and still attached to the catheter shaft 52.

Figure 3A:
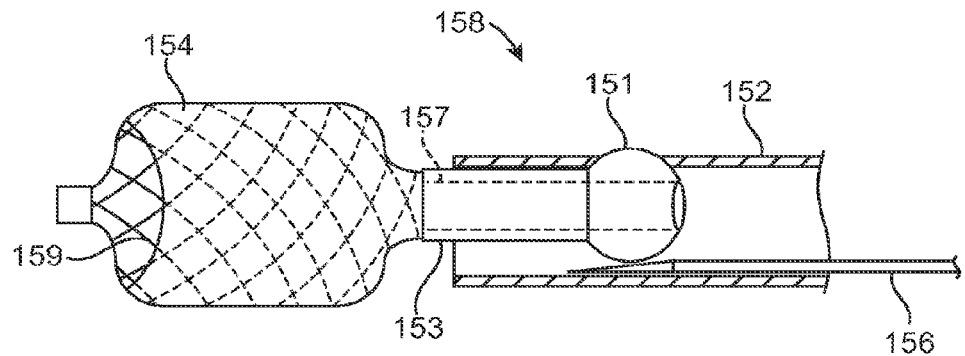
FIGS. 3A through 3C illustrate an exemplary release mechanism for selectively detaching a flow restrictive component from a catheter shaft.
Figure 3B:
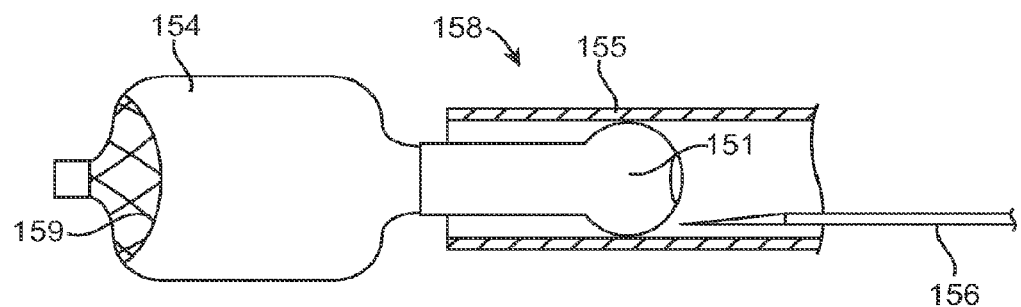
Figure 3C:
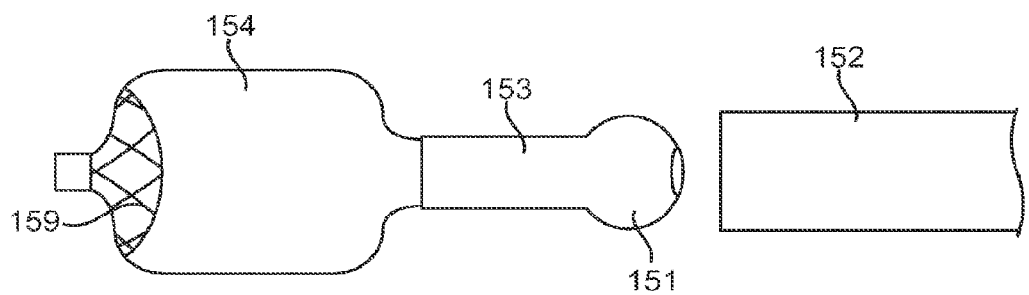

An exemplary release mechanism 158 for selectively detaching a flow restrictive component 154 from a catheter shaft 152 is illustrated in FIGS. 3A through 3C. The release mechanism 158 comprises a collar 153 attached at a proximal end of the self-expanding flow restrictive component 154. An attachment ball 151 projects from a proximal end of the sleeve 153. Both the attachment ball 151 and the sleeve 153 have an internal passage 157 which permits air flow through the release mechanism 158 so that air or other gases may be exchanged from the catheter shaft 152 through an open aperture 159 at a distal end of the flow restrictive component 154. The attachment ball 151 is received in an opening 155 (FIG. 3B) formed in a side of the shaft 152 and is held in place by a wire or other element having a tapered distal end which is wedged on a side of the ball opposite to the opening 155. So long as the wire 156 remains in place, as shown in FIG. 3A, the ball will be firmly held within the opening 155 and the flow restrictive component 154 will remain attached to the catheter shaft 152. The flow restrictive component 154 may be released, however, by withdrawing the wire 156, as shown in FIG. 3B, to allow the attachment ball 151 to be freed from the constraint of the hole 155. In this way, the flow restrictive component 154 may be completely released from the catheter shaft 152, as shown in FIG. 3C.

Figure 4A:
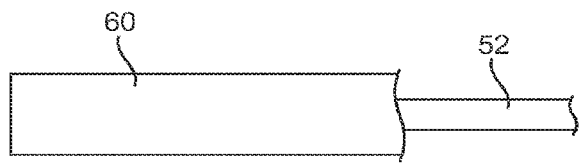
FIGS. 4A through 4D illustrate delivery and release of the flow restrictive component from the catheter of FIG. 3.
Figure 4B:
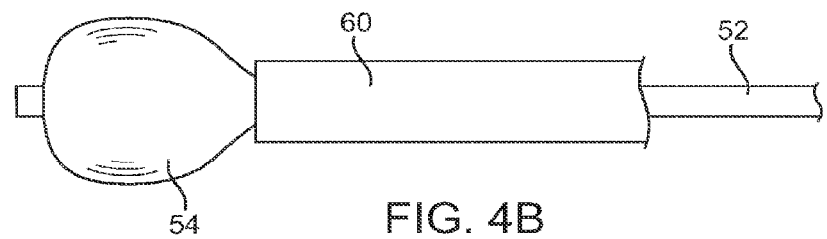
Figure 4C:
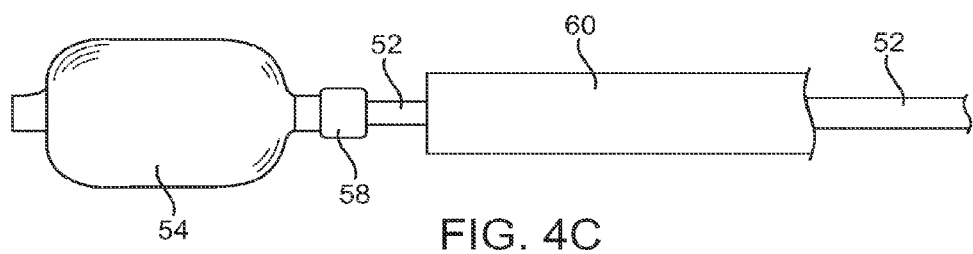
Figure 4D:
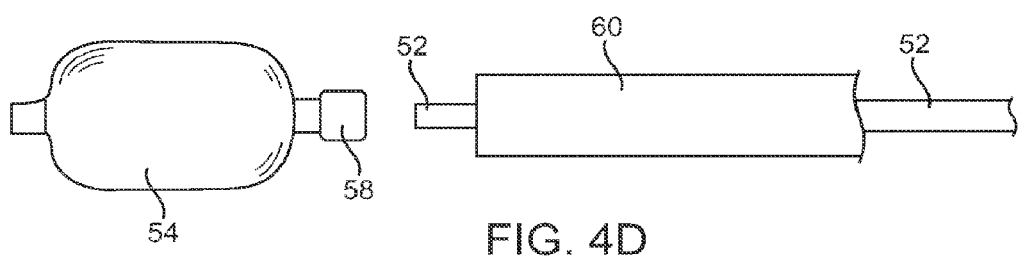

Usually, a separate delivery sheath 60 will be provided for facilitating delivery of the flow restrictive component 54 of the catheter 50. The sheath 60 will have a diameter 60 suitable for introduction into the target bronchii, typically having an outer diameter in the range from 1 mm to 3 mm. The flow restrictive component 54 will be radially constrained and introduced through an interior lumen of the delivery sheath, simply by pushing the shaft 52 distally so that the constrained flow restrictive component 54 is advanced through the sheath 50 as shown in FIG. 4A. Initially, the flow restrictive component 54 will be fully contained within the sheath 60. As the shaft 52 continues forward advancement, the flow restrictive component 54 will emerge from a distal end of the sheath 60, as shown in FIG. 4B. Upon further advancement, the flow restrictive component 54 will be fully released from the sheath, as shown in FIG. 4C. After performing a desired assessment of collateral ventilation or other lung compartment characteristic while the flow restrictive component 54 remains inflated and the lung compartment isolated, the flow restrictive component may be selectively released by actuating mechanism 58, as shown in FIG. 4D. After release, flow restrictive component 54 may be fully closed in order to provide for total occlusion of the bronchii in which it has been deployed. Alternatively, a smaller controlled flow path may remain through the flow restrictive component 54 in order to provide for controlled atelectasis or hypoxic pulmonary vasoconstriction (HPV), as described in copending application Ser. No. 11/682,986, the full disclosure of which has been previously incorporated herein by reference.

Specific examples of flow restrictive elements suitable for permitting continued air exchange with the isolated lung compartment and controlled atelectasis and/or HPV are illustrated in FIGS. 5-8.

Figure 5:
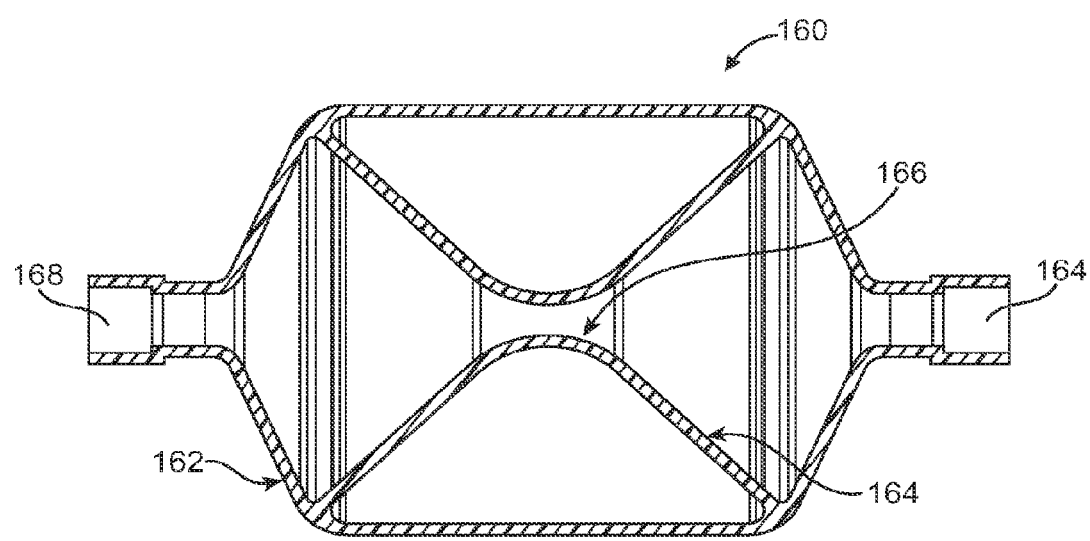
FIGS. 5-8 illustrate specific flow restrictive components useful with the catheter of FIG. 3.

FIG. 5 illustrates a flow restrictive component 160 in which a housing 162 houses a funnel-shaped (or hourglass-shaped) diaphragm 164 which provides a gas flow orifice 166 in the center of the diaphragm. Distal and proximal apertures 168 and 170, respectively, allow air flow into and out of the housing 162, and the tapered orifice 166 defined by the diaphragm 164 restricts the flow. The diameter of the orifice 166 can be selected to provide a desired flow resistance. The housing 162 can have a uni-body construction or be a wire braided structure encapsulated with silicone or other elastomere. The diaphragm can be a flexible silicone material or other elastomere in order to facilitate compressibility of the restrictor 160 for insertion into the lung via a delivery sheath lumen.

Figure 6:
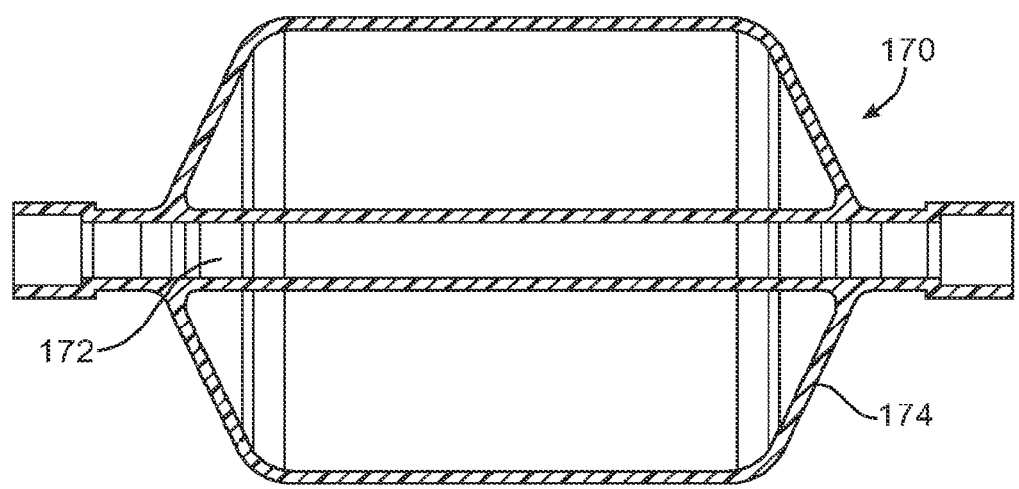

FIG. 6 illustrates flow restrictive component 170 in which a gas flow tube 172 is axially aligned in a housing 174. Construction of the housing 174 can be similar to any of the concepts previously described. The gas flow tube 172 can be constructed of any tubular material, preferably being a flexible polymer. Flexibility is advantageous since a flexible tube will facilitate insertion into the lung. The housing 174 can have any of the constructions described previously.

Figure 7:
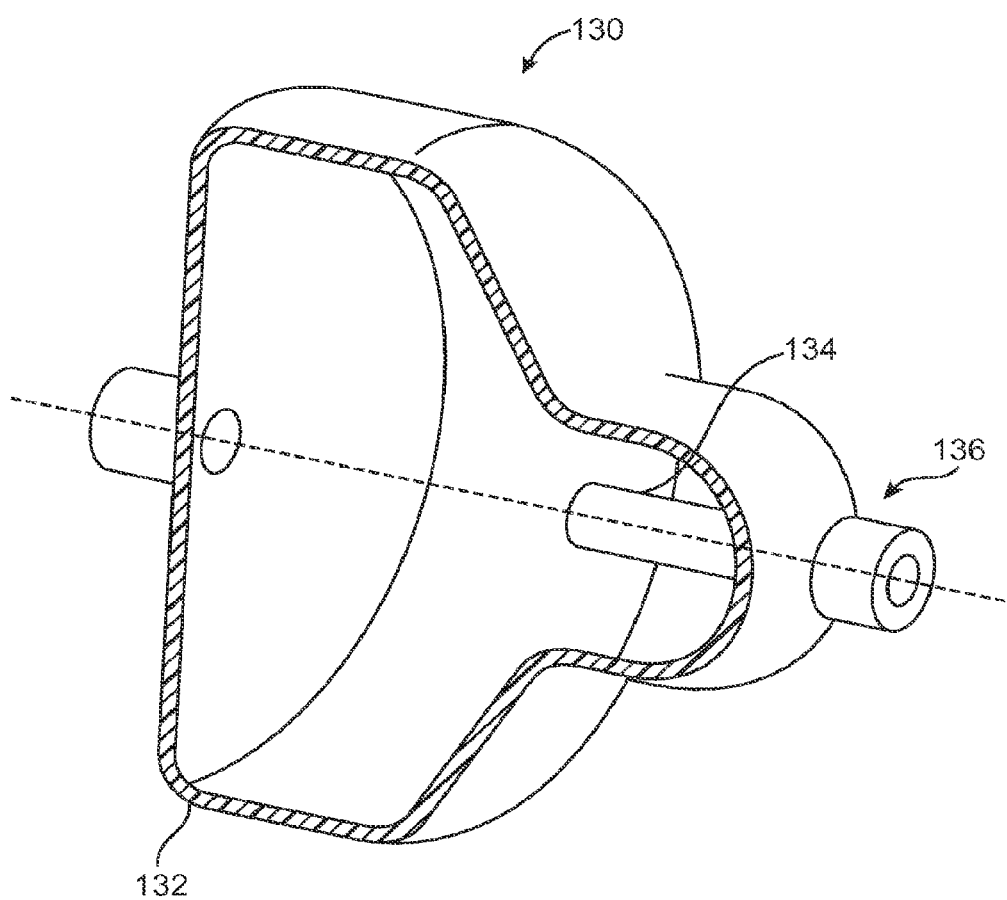

FIG. 7 is a cross-sectional view of a flow restrictive component 130 in which a housing 132 includes a gas flow orifice tube 134 on its distal end 136. The housing can have a "uni-body" construction, typically being molded or cast from silicone or another biocompatible elastomer. In some instances, the housing 132 can have composite construction of wire frame with silicone membrane coating, or be formed from a variety of materials and construction methods. It can be collapsible and self expanding for a catheter based delivery. In other designs, the flow restrictive component can be malleable to allow plastic deformation and expansion by a balloon or other expandable deployment on the delivery catheter.

Figure 8:
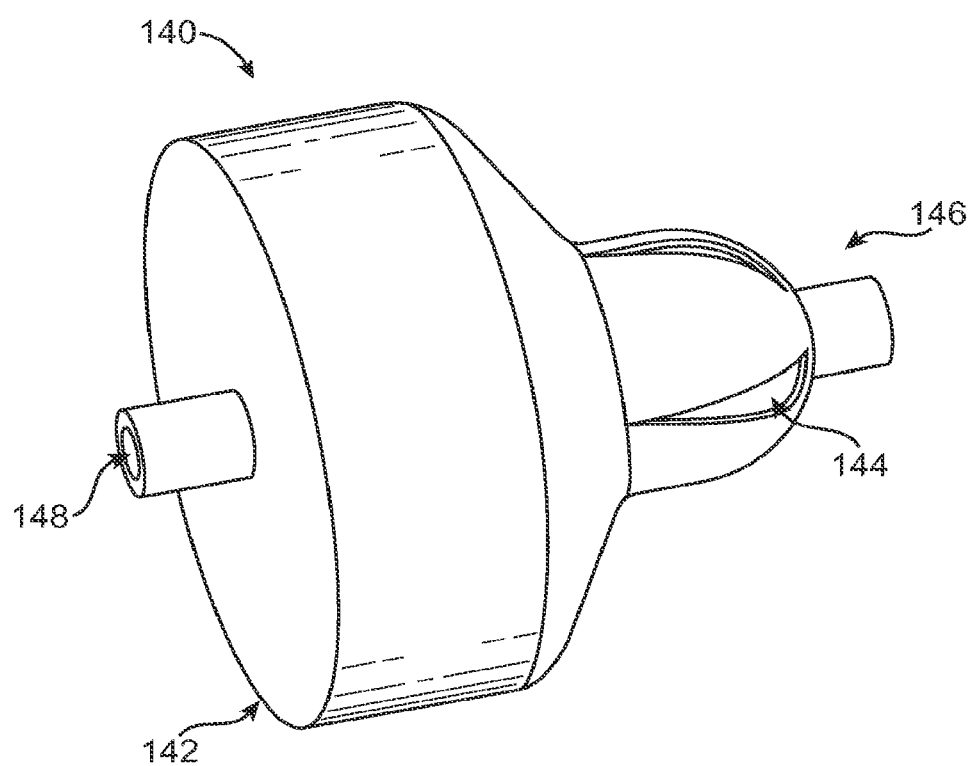

FIG. 8 illustrates a flow restrictive component 140 in which a housing 142 comprises a plurality of windows 144 in a wall of a distal section 46 in order to permit gas flow in and out of the housing. An orifice 148 at the opposite proximal end completes the gas flow path such that the device restricts but does not obstruct gas flow. As with previously described embodiments, the housing 142 can have a uni-body construction or comprise a wire frame with silicone or other membrane covering. It can be either collapsible and self expanding or balloon expandable.

Figure 9:
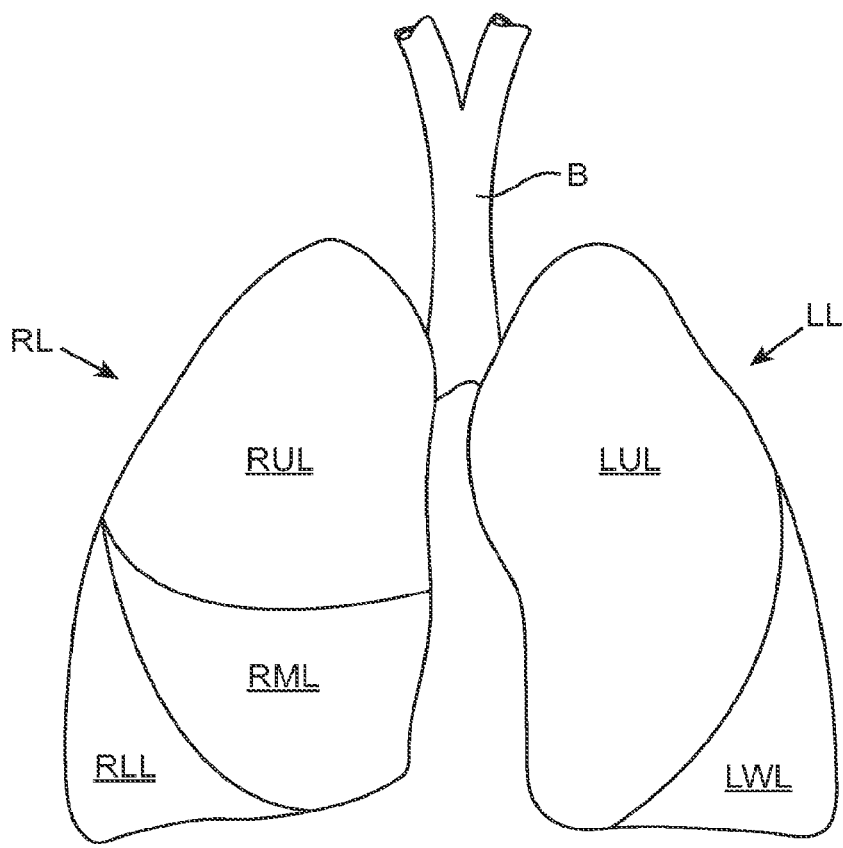
FIG. 9 is an anatomical diagram illustrating the lobar structure of the lungs of a patient.

Referring now to FIG. 9, the respiratory system of a patient starts at the mouth and extends through the vocal cords and into the trachea where it then joins the main stem bronchi B which leads into the right lung RL and the left lung LL. The bronchi going into the right lung divide into the three lobar bronchi which lead into the upper lobe RUL, the middle lobe RML and the lower lobe RLL. The lobes of the right lung include a total of ten segments (three in the RUL, two in the RML, and five in the RLL) which are discrete units of the lung separated from each other by a fibrous septum generally referred to as a lung wall. The left lung LL includes only an upper lobe LUL and a lower lobe LLL, where the individual lobes include four to five segments each.

Each lung segment, also referred to as a bronchopulmonary segment, is an anatomically distinct unit or compartment of the lung which is fed air by a tertiary bronchus and which oxygenates blood through a tertiary artery. Normally, the lung segment and its surrounding fibrous septum are intact units which can be surgically removed or separated from the remainder of the lung without interrupting the function of the surrounding lung segments. In some patients, however, the fibrous septum separating the lobes or segments may be perforate or broken, thus allowing air flow between the segments, referred to as "collateral ventilation."

Figure 10:
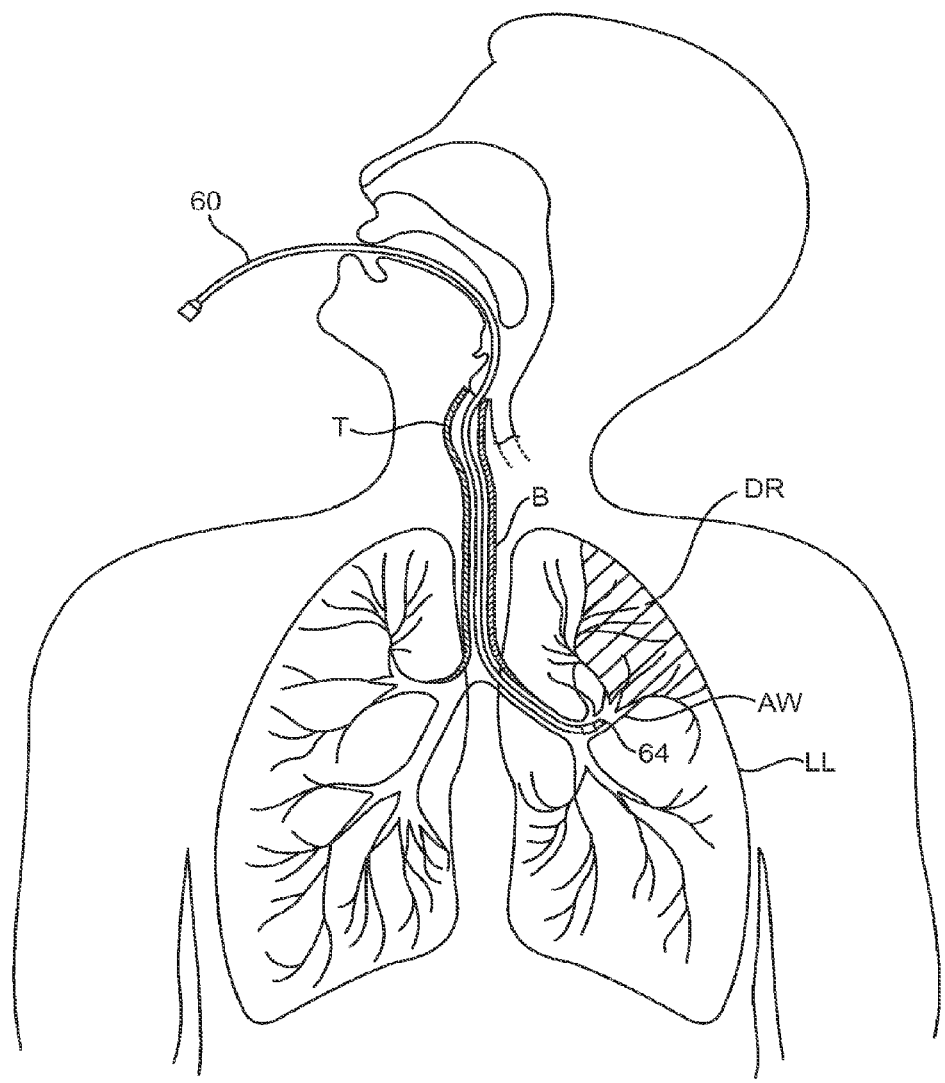
FIG. 10 illustrates the trans-esophageal endobronchial placement of the functional assessment and therapy catheter of the present invention in an airway leading to a diseased lung compartment.
Figure 11:
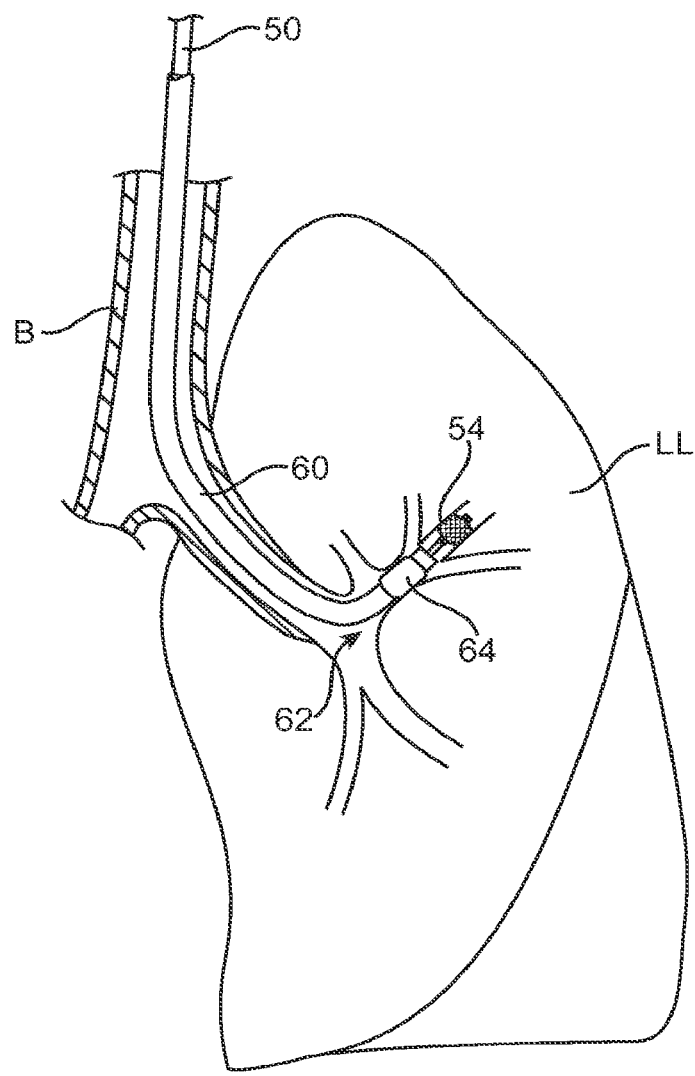
FIG. 11 illustrates the initial placement of a flow restrictive component in accordance with the principles of the methods of the present invention.

Use of the delivery sheath 60 for placement of the flow restrictive component 54 in accordance with the principles of the present invention shown generally in FIGS. 10-13. The sheath 60 is advanced through the mouth, down through the trachea T and through the main bronchus into the left lung LL. A distal end 62 of the sheath 60 is advanced into the left lung LL, and further advanced to an airway or bronchus which feeds a diseased lung region DR. The sheath 60 may be introduced through the main bronchus B and into the left lung LL without the use of a bronchoscope or other primary introducing catheter, as illustrated in FIG. 10. Alternatively, the sheath 60 may be introduced through a conventional bronchoscope (now shown) which is positioned in the main bronchus B above the branch between the right and left lungs. Still further alternatively, the sheath 60 may be introduced into the lung through a scope, such as a visualizing endotracheal tube (not shown) which is capable of being advanced into the branching bronchii of the lung and which may be advantageous since it facilitates positioning of the sheath 60 at the desired airway leading to the target diseased lung segment. Construction and use of a visualizing endotracheal tube is taught, for example, in U.S. Pat. No. 5,285,778, the full disclosure of which is incorporated herein by reference.

Figure 12:
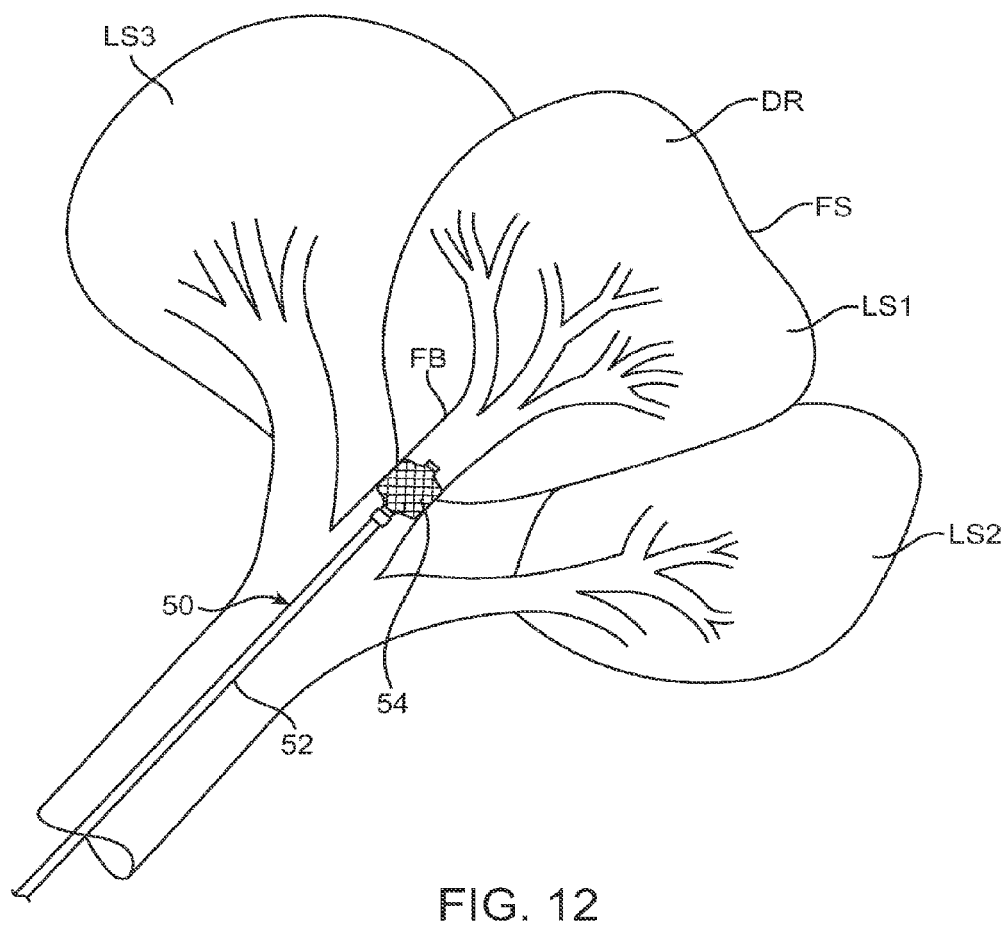
FIG. 12 illustrates the use of the functional assessment catheter for determining collateral ventilation.
Figure 13:
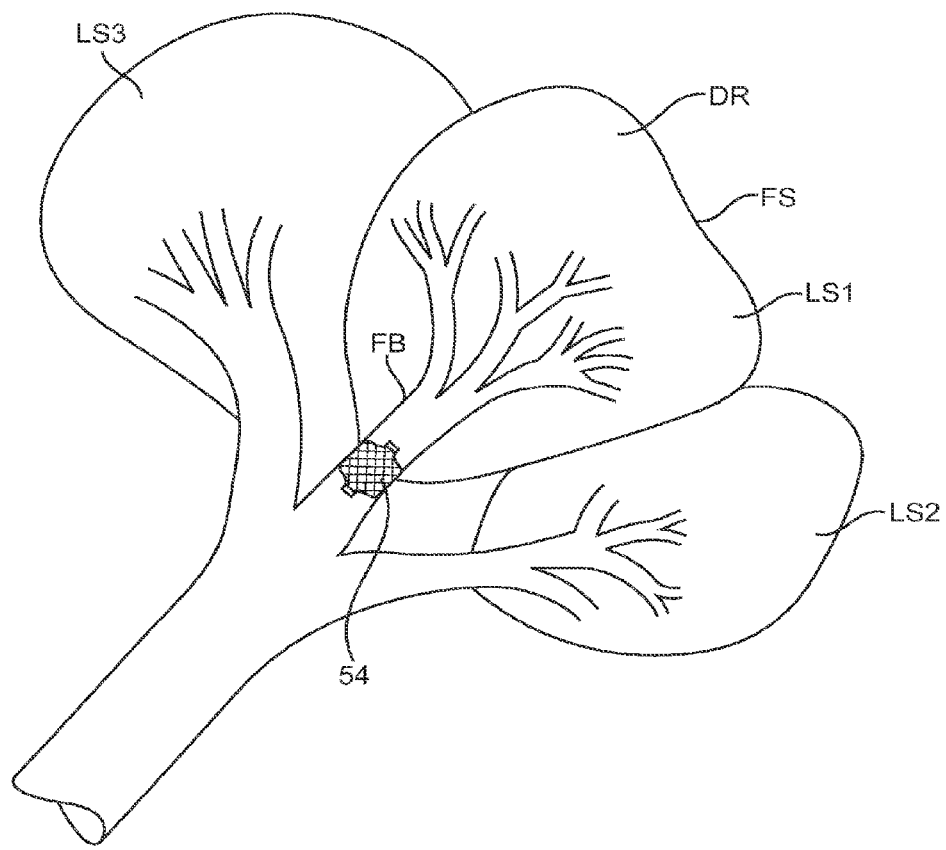
FIG. 13 illustrates release of the flow restrictive component into the lung passageway after it has been determined that collateral ventilation does not exist in the diseased lung compartment.

After the distal end 62 of the delivery sheath 60 has been positioned in the main airway or bronchus which feeds the diseased lung region DR, the sheath may be optionally immobilized by inflating a balloon or cuff 64 at or near the proximal end of the sheath 60. After immobilizing the distal end of the sheath, the catheter shaft 52 of catheter 50 may be distally advanced in order to deploy the flow restrictive component 54 into the feeding bronchus FB leading to the diseased lung region DR, as shown in FIG. 12. Once the flow restrictive component 54 is deployed, a diagnostic procedure for determining the extent and/or treatability of the disease may be performed, generally as described in previous application Ser. Nos. 11/296,951 and 11/550,660, the full disclosures of which have previously been incorporated herein by reference. If it is determined that the patient is suitable for treatment by an occlusive or flow restrictive protocol, the flow restrictive component 54 may be released and implanted in the feeding bronchus FB, as shown in FIG. 13. If, however, the patient is determined to be unsuitable for such treatment, the flow restrictive component 54 may be removed from the feeding bronchus FB, typically by retraction into the delivery sheath 60 and subsequent removal of the sheath from the lung.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A functional assessment catheter for the lungs, said catheter comprising:
    a catheter shaft having a distal and a proximal end, and a central passage there between;
    a flow restrictive component disposed at the distal end of the catheter shaft, wherein the flow restrictive component has an expanded configuration and a contracted configuration;
    an obturator disposed in the central passage and shiftable between a distally advanced position where it engages and elongates the flow restrictive component to cause the component to assume the contracted configuration, and a proximally retracted position where it allows the flow restrictive component to shorten and return to the expanded configuration; and
    a release mechanism for selectively detaching the flow restrictive component from the catheter shaft; wherein the release mechanism comprises a sleeve attached at a proximal end of the flow restrictive component and an attachment ball projects from a proximal end of the sleeve, wherein both the attachment ball and the sleeve have an internal passage which permits air flow through the release mechanism so that gases may be exchanged from the catheter shaft through an open aperture at a distal end of the flow restrictive component to permit performance of a diagnostic test for collateral ventilation.

2. A functional assessment catheter as in claim 1, wherein the flow restrictive component comprises a resilient scaffold and an elastomeric covering.

3. A functional assessment catheter as in claim 2, wherein the resilient scaffold comprises counter wound helical supports.

4. A functional assessment catheter as in claim 1, wherein a flow path is formed through the flow restrictive component so that gas may flow through the catheter shaft and through the flow restrictive component.

5. A functional assessment catheter as in claim 4, wherein the flow path comprises the catheter shaft and an opening in a distal side of an elastomeric covering of the flow restrictive component.

6. A functional assessment and treatment catheter for the lungs, said catheter comprising:
    a catheter shaft having a distal end, a proximal end, and a central lumen therethrough;
    and a detachable flow restrictive component releasably secured to the distal end of the catheter shaft, said flow restrictive component having an expanded configuration for sealing to an inner wall of a lung passage and a contracted configuration to permit positioning within the lung passage; and a release mechanism for selectively detaching the flow restrictive component from the catheter shaft; wherein the release mechanism comprises a sleeve attached at a proximal end of the flow restrictive component and an attachment ball projects from a proximal end of the sleeve, wherein both the attachment ball and the sleeve have an internal passage which permits air flow through the release mechanism;

wherein the catheter shaft, release mechanism and flow restrictive component together permit gas exchange therethrough with a lung compartment distal to the flow restrictive element while the flow restrictive element is expanded within a main bronchus leading to said lung compartment to permit performance of a diagnostic test for collateral ventilation.

7. A functional assessment and treatment catheter as in claim 6, further comprising an obturator disposed in the central passageway, and shiftable between a distally advanced position where it engages and elongates the flow restrictive component to cause the component to assume the contracted configuration, and a proximally retracted position where it allows the flow restrictive component to shorten and return to the expanded configuration.

8. A functional assessment and treatment catheter as in claim 6, further comprising a constraining structure configured to slide over and radially constrain the flow restrictive component.

9. A functional assessment and treatment catheter as in claim 6, wherein the flow restrictive component comprises a resilient scaffold and an elastomeric covering.

10. A functional assessment and treatment catheter as in claim 9, wherein the resilient scaffold comprises counter wound helical supports.

11. A functional assessment and treatment catheter as in claim 6, wherein a flow path is formed through the flow restrictive component so that gas may flow through the catheter shaft and through the flow restrictive component.

12. A functional assessment and treatment catheter as in claim 11, wherein the flow path comprises the central lumen and an opening in a distal side of an elastomeric covering of the flow restrictive component.

* * * * *